United States Patent
Ueyama et al.

(10) Patent No.: US 6,620,164 B2
(45) Date of Patent: Sep. 16, 2003

(54) ROD FOR CERVICAL VERTEBRA AND CONNECTING SYSTEM THEREOF

(75) Inventors: Kazumasa Ueyama, Aomori-ken (JP); Akio Sannohe, Aomori-ken (JP); Naoki Echigoya, Aomori-ken (JP); Kazuya Oribe, Tokyo (JP); Noriyuki Ina, Aichi-ken (JP)

(73) Assignee: Showa Ika Kohgyo Co., Ltd., Aichi-ken (JP)

( * ) Notice: Subject to any disclaimer, the term of this patent is extended or adjusted under 35 U.S.C. 154(b) by 12 days.

(21) Appl. No.: 09/955,943

(22) Filed: Sep. 20, 2001

(65) Prior Publication Data
US 2002/0042614 A1 Apr. 11, 2002

(30) Foreign Application Priority Data

Sep. 22, 2000 (JP) .................................. P2000-289284
Oct. 2, 2000 (JP) .................................. P2000-302544

(51) Int. Cl.⁷ .............................................. A61B 17/70
(52) U.S. Cl. ........................... 606/61; 606/606; 606/72
(58) Field of Search ............................. 606/61, 60, 69, 606/72, 71, 73, 53, 86

(56) References Cited

U.S. PATENT DOCUMENTS

| 4,987,892 A | * | 1/1991 | Krag et al. ................ 606/61 |
| 5,306,275 A | | 4/1994 | Bryan |
| 5,360,429 A | * | 11/1994 | Jeanson et al. ............ 606/61 |
| 5,395,370 A | | 3/1995 | Müller et al. |
| 5,498,262 A | | 3/1996 | Bryan |
| 5,520,689 A | | 5/1996 | Schläpfer et al. |
| 5,643,263 A | * | 7/1997 | Simonson .................. 606/61 |
| 5,725,582 A | | 3/1998 | Bevan et al. |
| 5,810,816 A | * | 9/1998 | Roussouly et al. ......... 606/61 |
| 5,885,285 A | * | 3/1999 | Simonson .................. 606/61 |
| 5,947,965 A | | 9/1999 | Bryan |
| 6,077,262 A | | 6/2000 | Schläpfer et al. |
| 6,077,263 A | | 6/2000 | Ameil et al. |
| 6,287,309 B1 | * | 9/2001 | Baccelli et al. ............ 606/61 |
| 6,488,685 B1 | * | 12/2002 | Manderson ................ 606/69 |

FOREIGN PATENT DOCUMENTS

EP          0743045          11/1996

* cited by examiner

*Primary Examiner*—Pedro Philogene
(74) *Attorney, Agent, or Firm*—Greenblum & Bernstein, P.L.C.

(57) ABSTRACT

Connector connecting an implant to a bone connecting rod. The connector includes a first fastening member provided with an engagement hole freely engaging with a head portion of the implant anchored to the vertebral bodies and a fastening groove. A second fastening member is provided with an insertion hole freely inserting the rod therethrough and a fastening groove. A through hole penetrating in a direction crossing to the fastening groove in the first fastening member and a through hole penetrating in a direction crossing to the fastening groove in the second fastening member are provided with fastening devices.

7 Claims, 8 Drawing Sheets

FIG.6A
FIG.6B
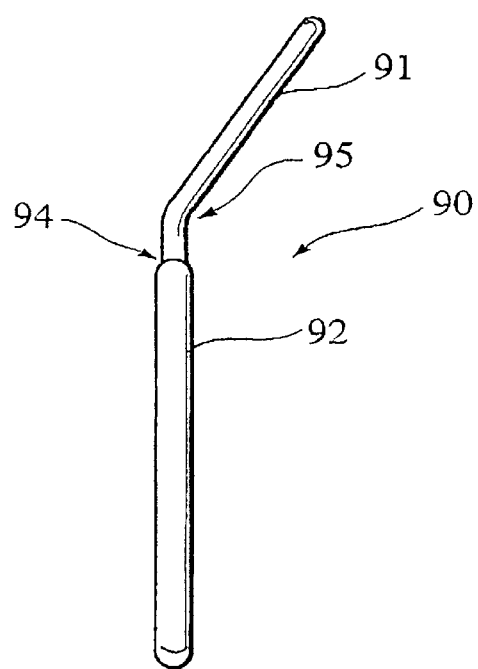
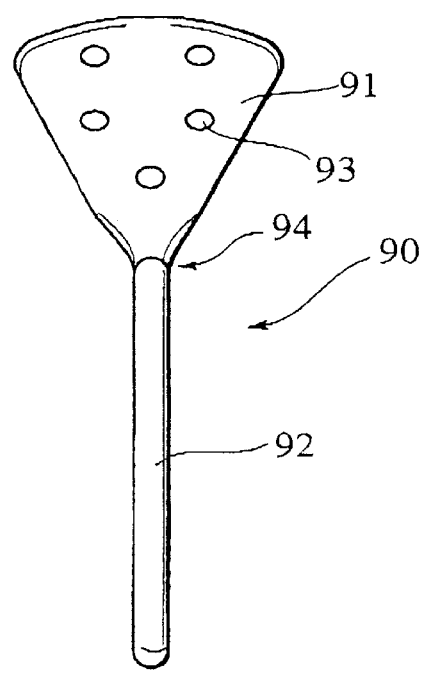

ROD FOR CERVICAL VERTEBRA AND CONNECTING SYSTEM THEREOF

BACKGROUND OF THE INVENTION

1. Field of the Invention

The present invention relates to a rod plate for a cervical vertebra which connects and bonds a cranium portion and a cervical vertebra portion, and a connector for connecting them. More particularly, the present invention relates to a rod plate for a cervical vertebra which can easily mount to the cranium portion, and a connector which can set a mounting angle of the rod plate for the cervical vertebra and an implant to a desired angle.

2. Description of the Related Art

As a structure of a connector for a rod plate and a structure of the rod plate according to the related art, there are structures shown in FIGS. 1, 2 and 3.

At first, the related art concerning the connector portion will be described with reference to FIGS. 1 and 2. The structure is made such that a flat portion 5 is provided in a head portion of a screw portion 3 screwed and inserted as an implant screwed and inserted to a body of vertebra in a vertebral bone, and a U-shaped groove 7 is provided in the flat portion.

Then, a connector 11 for connecting a bone connecting rod 9, for example, connecting a vertebral bone and a vertebral bone and the implant 1 described above is provided with a connector main body 15 having an oblong through hole 13 freely inserting through the rod 9. A protruding portion 17 freely engaged with and disengaged from the U-shaped groove 7 of the implant 1 is provided in the connector main body 15, and a semicolumnar engaging portion 19 which is slightly longer in the same direction as a penetrating direction of the through hole 13 is provided at a front end of the protruding portion 17.

A rectangular portion 21 is formed in a side of the protruding portion 17 of the connector main body 15, and an annular lock member 23 is slidably fitted and supported to the rectangular portion 21. A lot of radial grooves are formed on a contact surface on which the lock member 23 is brought into contact with the flat portion 5 in the implant 1, around an axis of the protruding portion 17, whereby a concavo-convex surface 25 is formed, and a contact surface 5a of the flat portion 5 in the implant 1 is formed in the similar concavo-convex surface.

In order to fasten and fix the rod 9 inserted to the through hole 13, a screw hole 31 freely screwing a fastening screw 27 is provided in the connector main body 15. The screw hole 31 is formed in an inclined manner with respect to the through hole 13 in such a manner as to press the rod 9 in a direction of the lock member 23 by the front end portion of the screwed fastening screw 27.

Accordingly, when engaging the protruding portion 17 of the connector main body 15 with the U-shaped groove 7 of the implant 1, positioning the flat portion 5 of the implant 1 between the engaging portion 19 and the lock member 23, inserting the rod 9 to the through hole 13 and thereafter fastening the fastening screw 27, the rod 9 is moved in the direction of the lock member 23 by the front end portion of the fastening screw 27, the concavo-concave surface 25 of the lock member 23 is brought into contact with the contact surface 5a of the flat portion 5 in the implant 1 and the concave-convex surfaces are engaged with each other, so that it is possible to fix the rod 9 to the implant 1.

Next, the related art of the rod plate for the cervical vertebra connected to the above connector will be described with reference to FIG. 3.

A fixing device 86 is structured such as to be provided with a mounting portion 81 to a cranium portion 85 and a mounting portion 83 to a cervical vertebra 82, the mounting portion 83 to the cervical vertebra 82 is formed in a rod shape, and the mounting portion 81 to the cranium portion 85 is formed in a flat shape. Further, the flat mounting portion 81 is suitably bent with respect to the rod-shaped mounting portion 83 and is bent in a circular arc shape so as to be asymmetrical.

The rod-shaped mounting portion 83 is integrally supported and fixed to a supporting and fixing device 84 suitably mounted to the cervical vertebra 82, and is integrally fixed to the flat-shaped mounting portion 81 in the cranium 85 by inserting the screw 80 to the mounting hole provided in the mounting portion 81 and screwing to the cranium 85.

In the connector structure as described above, since the structure is made such as to press the lock member 23 via the rod 9, it is impossible to stably mount the connector main body 15 to the implant 1 in a state that the rod 9 is not inserted to the through hole 13 of the connector main body 15, so that there is a problem that it is hard to set the connector, Moreover, in the structure of the rod plate connected to the connector described above, since the shapes are different between right and left, it is necessary to properly use the right and left parts and it is necessary to independently manufacture them, so that it is hard to manufacture them. Further, there is a problem that it is not easy to align the longitudinal direction of the rod-shaped mounting portion with the supporting and fixing device.

SUMMARY OF THE INVENTION

The present invention is made by taking the problems in the related art as described above into consideration. According to a first aspect of the present invention, there is provided a connector connecting an implant screwed and inserted to a body of vertebra to a bone connecting rod, comprising: a first fastening member provided with an engagement hole freely engaging with a head portion of the implant and a fastening groove; and a second fastening member provided with an insertion hole freely inserting the rod therethrough and a fastening groove, wherein a through hole penetrating in a direction crossing to the fastening groove in the first fastening member and a through hole penetrating in a direction crossing to the fastening groove in the second fastening member are provided with fastening devices freely penetrating.

Moreover, in the connector described above, the structure may be made such that the fastening device is a bolt, and a screw hole portion freely engaging with the bolt is formed in one end side of the through hole in the first fastening member or in one end side of the through hole in the second fastening member.

Moreover, in the connector described above, the structure may be made such that plural kinds of tool engagement portions are provided in a head portion of the bolt.

Moreover, in the connector according to the first aspect, the structure is made such that a plurality of engagement portions are provided in a circular arc direction around the through hole, on a connecting surface between the first fastening member and The second fastening member, whereby an angle adjusting and engaging portion is provided.

A rod plate according to the present invention is a cervical vertebra rear portion fixing device in which a mounting portion to a cervical vertebra is formed as a rod portion, a mounting portion to a cranium portion is formed in a flat and substantially fan shape, and a plurality of mounting holes are provided in the flat-shaped mounting portion, wherein the flat-shaped mounting portion is formed to be symmetrical and a plurality of mounting holes are arranged In a symmetrical manner so as to be formed to be common between the right and left sides.

In a system connecting a rod plate for a cervical vertebra in which a mounting portion to a cervical vertebra is formed as a rod portion, a mounting portion to a cranium portion is formed in a flat shape, a plurality of mounting holes are provided in the flat-shaped mounting portion, the flat-shaped mounting portion is formed to be symmetrical, and a plurality of mounting holes are arranged in a symmetrical manner so as to be formed to be common between the right and left sides, to an implant screwed and inserted to a body of vertebra, the structure may be made such that the system is provided with a first fastening member having an engagement hole freely engaging with a head portion of the implant and a fastening groove, a second fastening member provided with an insertion hole freely inserting the rod portion therethrough and a fastening groove, further, the structure may be made such that a through hole penetrating in a direction crossing to the fastening groove in the first fastening member and a through hole penetrating in a direction crossing to the fastening groove in the second fastening member are provided with fastening devices freely penetrating.

BRIEF DESCRIPTION OF THE DRAWINGS

FIG. 6A is a side view of a rod plate for a cervical vertebra according to the present invention;

FIG. 6B is a front elevational view of the rod plate for the cervical vertebra according to the present invention;

DETAILED DESCRIPTION OF THE PREFERRED EMBODIMENT

Hereinafter, embodiments according to the present invention will be described with reference to FIGS. 4A to 8.

"Connector"

<First Embodiment>

Figure 1:
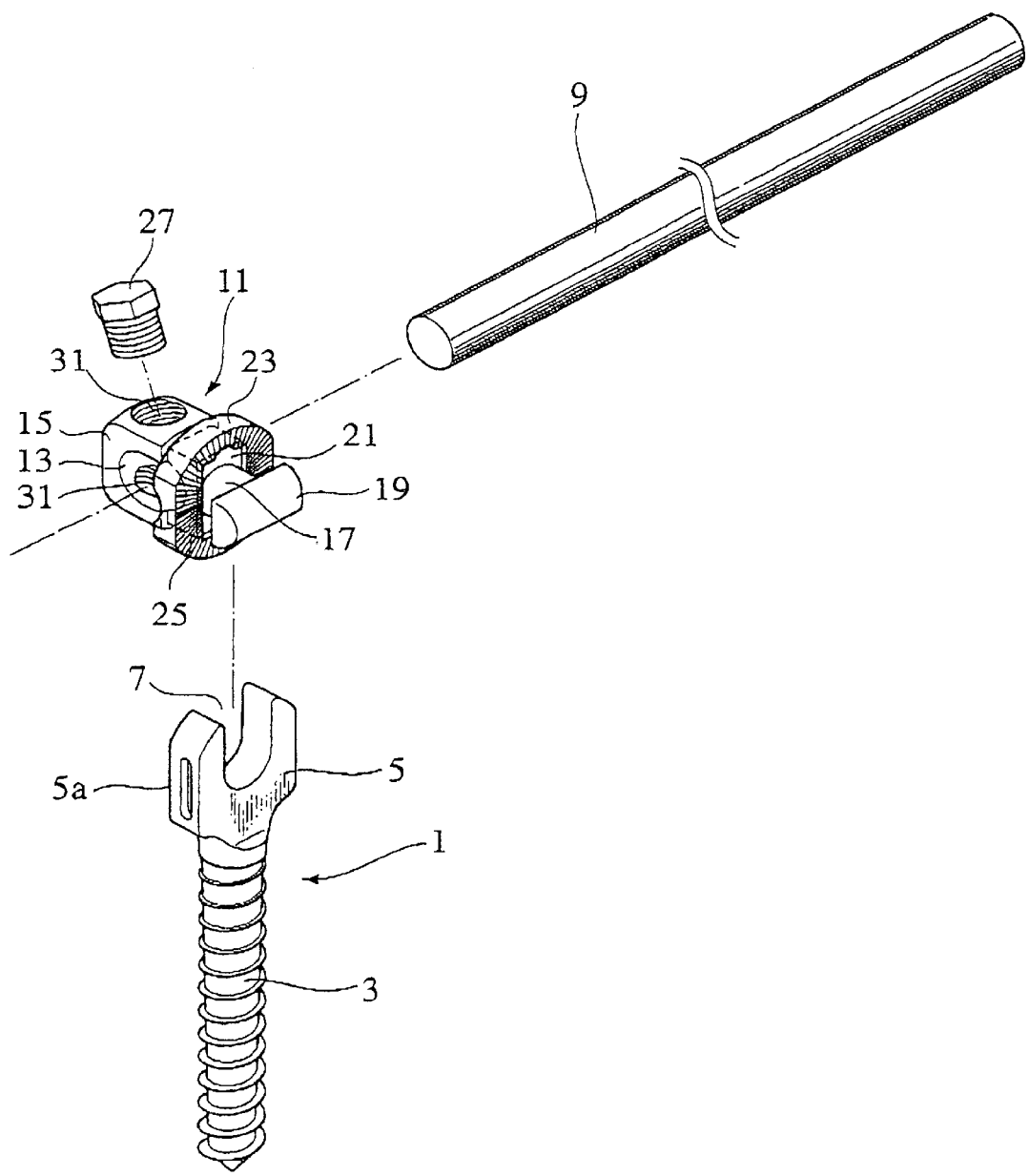
FIG. 1 is a perspective explanation view showing a connector.
Figure 2:
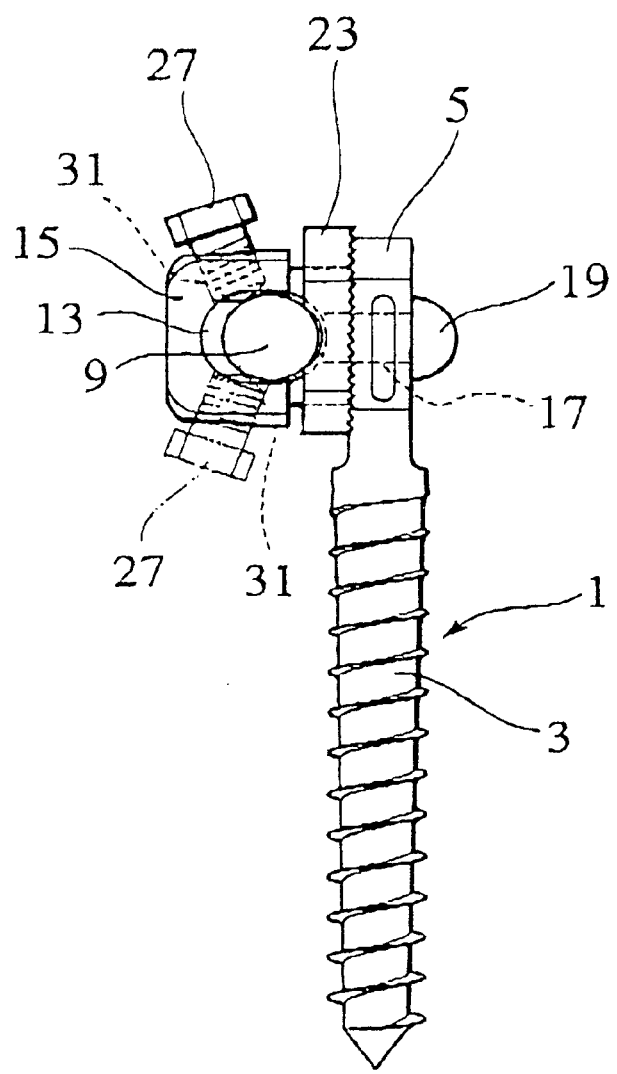
FIG. 2 is a explanation view showing an assembled state of the connector.
Figure 3:
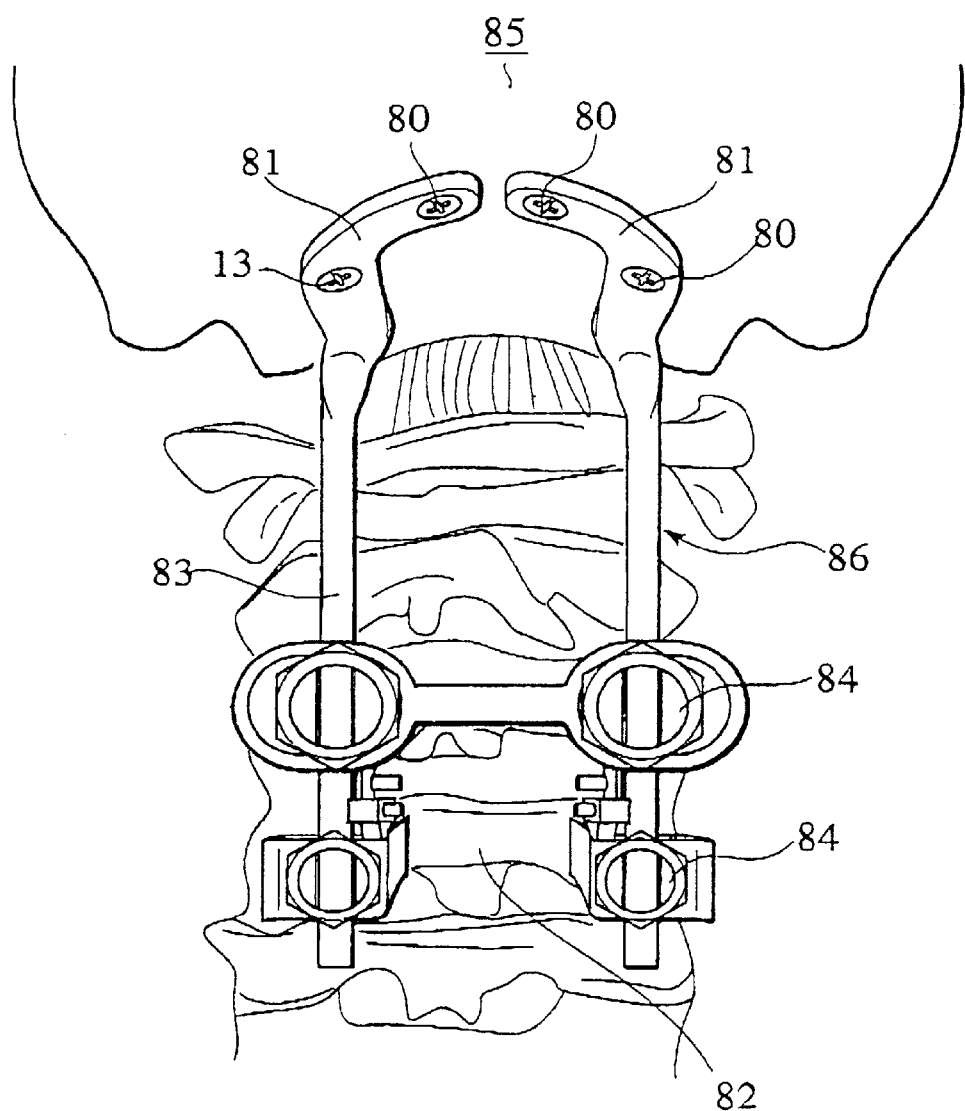
FIG. 3 is a explanation view of an example of how a rod plate for a cervical vertebra is used.
Figure 4A:
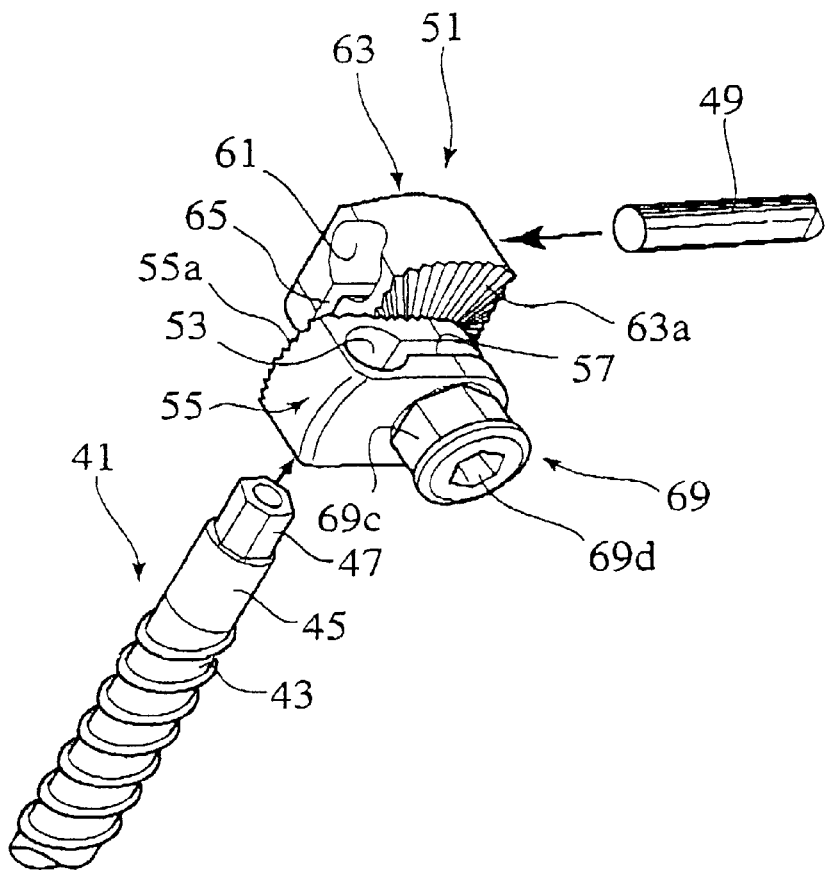
FIG. 4A is a perspective view of a connector according to a first embodiment of the present invention.
Figure 4B:
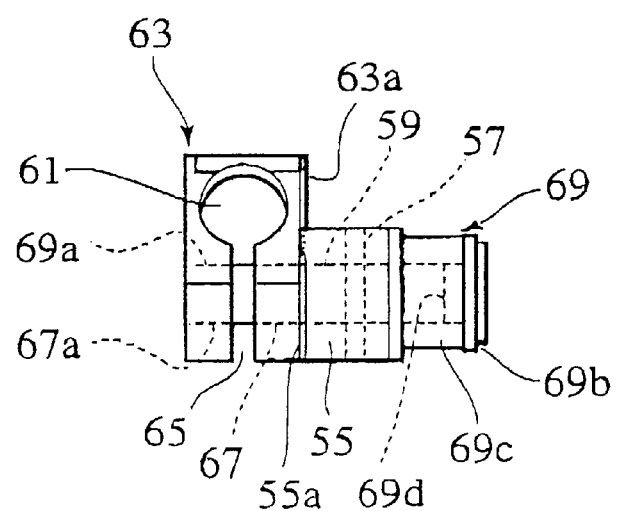
FIG. 4B is a front elevational view of the connector according to the first embodiment of the present invention.

With reference to FIG. 4A, an implant 41 screwed and inserted to a body of vertebra of a vertebral bone is formed in a pipe shape provided with a through hole in an axial core portion, a cylindrical portion 45 is provided in a head portion of a screw portion 43 screwed and inserted to the body of vertebra of the vertebral bone, and a polygonal tool engagement portion 47 is formed in a top portion of the cylindrical portion 45.

A connector 51 for connecting a bone connecting rod 49 connecting the rod portion in another end side of the cervical vertebra rod plate, for example, fixing one end portion to the cranium or between the vertebral bone and the vertebral bone, to the implant 41 is provided with a main body for an implant 55 having an engagement hole 53 freely engaged with the circular portion 45 of the head portion in the implant 41, and a fastening groove (slit) 57 for fastening and fixing the implant 41 engaged with the engagement hole 53 is provided in the implant main body 55 so as To be communicating with the engagement hole 53. The implant main body 55 constitutes a first fastening member for being fastened and integrally formed with the implant 41, and a through hole 59 is provided in a direction crossing to the fastening groove (slit) 57, that is, in a vertically crossing direction.

A rod main body 63 provided with an insertion hole 61 freely inserting the rod 49 therethrough constitutes a second fastening member having the substantially same structure as that of the implant main body 55, and in order to fasten and fix the rod 49 inserted to the insertion hole 61, a fastening groove (slit) 65 is provided so as to be communicating with the insertion hole 61. Further, a through hole 67 is provided in a direction crossing to the slit 65, that is, a vertically crossing direction, and a screw hole portion 67a is formed in one end side of the through hole 67.

The implant main body 55 and the rod main body 63 are integrally connected by a fastening bolt 69 corresponding to a fastening device which penetrates the through hole 59 formed in the implant main body 55 and screwed with a screw hole portion 67a of the through hole 67 in the rod main body 63 at a front end portion.

A lot of concavo-convex portions are formed by forming a lot of radial grooves around the through holes 59 and 67 on respective connecting surfaces 55a and 63a or the implant main body 55 and the rod main body 63. Accordingly, the implant main body 55 and the rod main body 63 can be adjusted at a desired angle and be connected to each other in a immobile state. In this case, the description is given of a case that a lot of grooves are formed in a radial direction as an angle adjusting and engaging portion freely adjusting an angle, however, the structure may be made such that a lot of recess portions (for example, grooves) are formed on a circular arc around the through hole on one connecting surface, and convex portions (for example, a suitable number of protrusions engaging with the grooves) freely engaging with the recess portions are formed on another connecting surface. The fastening bolt 69 corresponding to one example of the fastening device is provided with a screw portion 69a penetrating the through holes 59 and 67 so as to be freely engaged with and inserted to the screw hole portion 67a, and a first tool engagement portion 69c formed in a polygonal shape on an outer peripheral surface is provided in a head portion 69b thereof, and a tool engagement hole formed in a non-circular shape such as an oval or a polygonal shape is formed in an axial portion of a top surface so as to constitute a second tool engagement portion 69d.

<Second Embodiment>

Figure 5A:
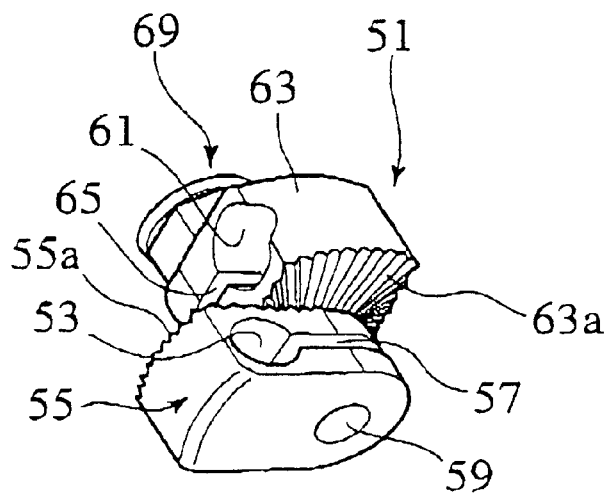
FIG. 5A is a perspective view of a connector according to a second embodiment of the present invention.
Figure 5B:
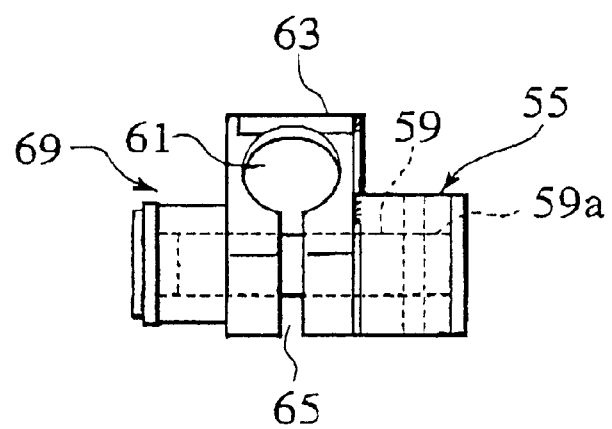
FIG. 5B is a front elevational view of the connector according to the second embodiment of the present invention.
Figure 7:
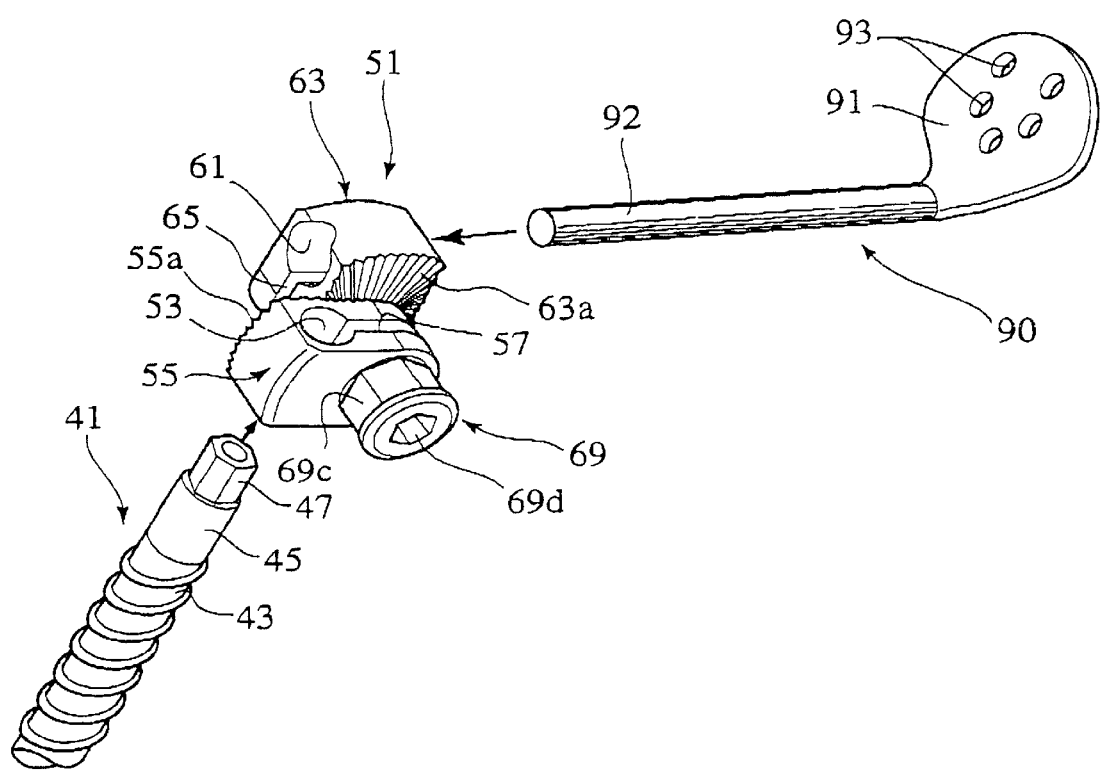
FIG. 7 is a perspective schematic view showing a relation among the rod plate for the cervical vertebra, the connector and an implant according to the present invention.
Figure 8:
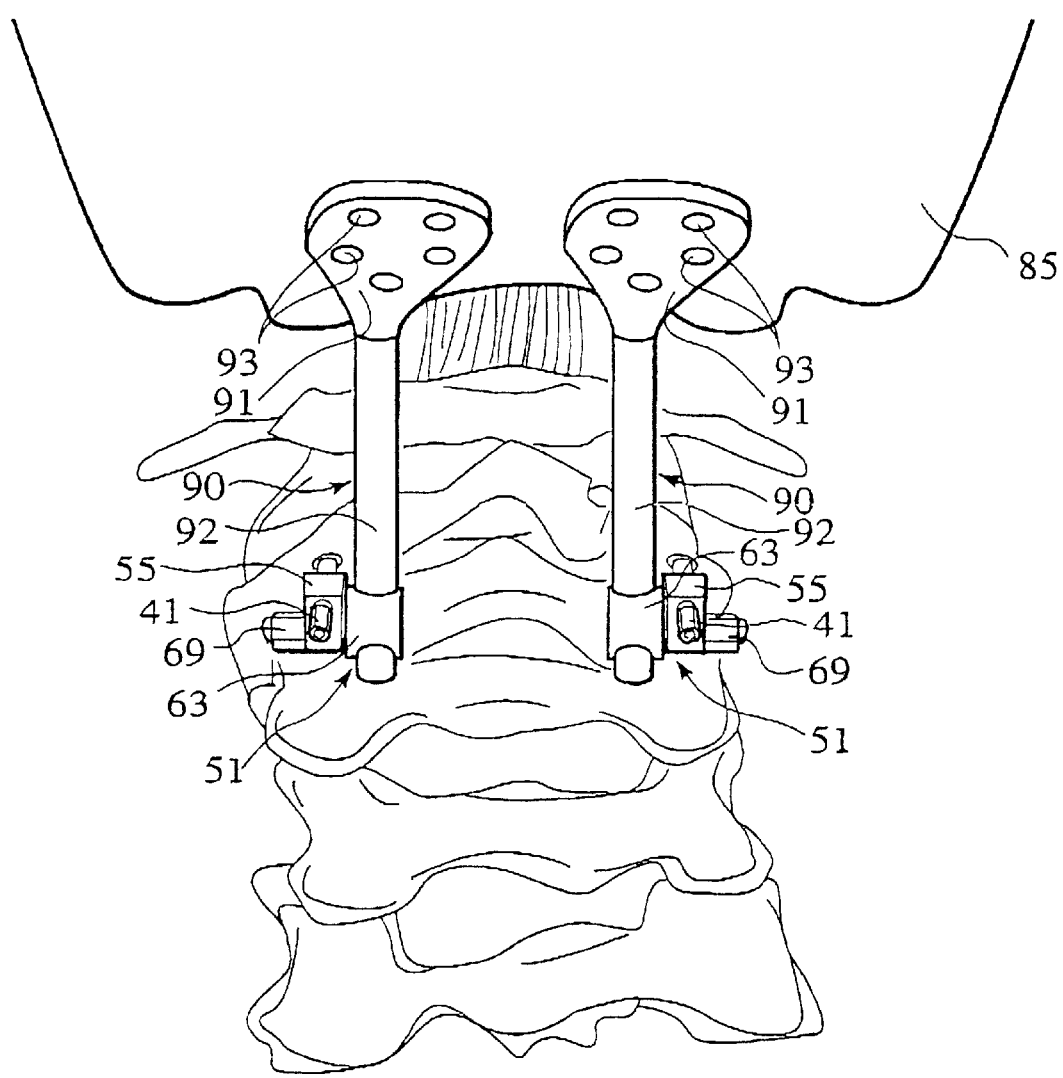
FIG. 8 is a schematic view of an example of how the rod plate for the cervical vertebra according to the present invention is used.

FIGS. 5A and 5B show a second embodiment of a connector according to the present invention. Since the screw hole portion 59a with which the front end portion of the fastening bolt 69 is engaged is provided in one end side of the through hole 59 in the implant main body 55, and the other structures are the same as the structures described above, the same reference numerals are attached to the same elements as those having the same functions and an overlapping description will be omitted.

As is understood from the above description, according to the second embodiment, since it is possible to rotate and adjust the implant main body 55 with respect to the implant 41, it is not necessary to align a directionality with the implant 41, and it is possible to easily align the insertion hole 61 in the rod main body 63 with the direction of the rod 49. Then, it is possible to rotate and adjust the rod main body 63 around the fastening bolt 69 with respect to the implant main body 55 and it is possible to easily coincide an axis of the insertion hole 61 in the rod main body 63 with an axis of the rod 49.

Accordingly, it is possible to easily connect the implant 41 to the rod 49.

"Rod Plate"

Next, a rod plate for a cervical vertebra according to the present invention will be described with reference to FIGS. 6A to 8.

With reference to FIGS. 6A and 6B, a rod plate for a cervical vertebra 90 according to an embodiment of the present invention is structured such that a mounting portion 92 to a cervical vertebra portion is formed in a rod portion and a mounting portion 91 to a cranium 85 portion connected to the rod portion is inclined with respect to a bent portion 95 corresponding to a supporting point. Moreover, the mounting portion 91 is formed in a flat substantially fan shape at an upper portion from a boundary portion 94 with the rod portion, and is formed in a substantially symmetrical shape. Moreover, a plurality of mounting holes 93 provided in the mounting portion 91 are arranged in a substantially symmetrical shape. Accordingly, at a time of fixing the flat mounting portion 91 to the cranium 85, it is possible to commonly use the right and left sides and it Is possible to easily fix by screwing and inserting a screw (not shown) to the cranium 85 through a necessary mounting hole 93.

The rod plate for the cervical vertebra 90 is fixed to the cervical vertebra via the connector 51 mounted to the implant 41 screwed and inserted to the body of vertebra of the cervical vertebra.

"Connection between Implant and Rod"

In the structure described above, as shown in FIGS. 7 and 8, in order to connect the implant 41 screwed and inserted to the body of vertebra of the cervical vertebra to the rod-shaped mounting portion 92 of the rod plate for the cervical vertebra 90 fixing the flat-shaped mounting portion 91 in one end side to the cranium 85, at first, the cylindrical portion 45 of the implant 41 is engaged with the engagement hole 53 of the implant main body 55 in a state of loosening the fastening bolt 69.

In this state, it is possible to rotate and adjust the implant main body 55 with respect to the implant 41 around the implant 41 in a desired direction, and it is possible to align the insertion hole 61 of the rod main body 63 in the direction of the rod-shaped mounting portion 23. It is possible to coincide the insertion hole 61 in the rod main body 63 with the axis of the rod-shaped amounting portion 23 rotating the rod main body 63 with respect to the implant main body 55 around the fastening bolt 69, and it is possible to easily insert and engage the mounting portion 23 with respect to the insertion hole 61.

In a state that the cylindrical portion 45 of the implant 41 is engaged with the engagement hole 53 of the implant main body 55 in the manner described above and the rod-shaped mounting portion 23 is inserted to the insertion hole 61 of the rod main body 63, by fastening the fastening bolt 69, the fastening groove 65 of the rod main body 63 and the fastening groove 57 of the implant main body 55 are fastened, whereby the implant 41 and the cervical vertebra rod plate 90 are integrally connected and fixed. At this time, the implant main body 55 and the rod main body 63 are fixed in an immobile state due to an engagement between the concavo-concave portions formed on the mutual connecting surfaces 55a and 63a.

As is understood from the above description, since it is possible to rotate and adjust the implant main body 55 with respect to the implant 41, it is unnecessary to align the directionality with respect to the Implant 41, and it is possible to easily align the insertion hole 61 in the rod main body 63 with the direction of the rod-shaped mounting portion 92 of the cervical vertebra rod plate 90. It is possible to rotate and adjust the rod main body 63 with respect to the implant main body 55 around the fastening bolt 69, and it is possible to easily coincide the axis of the insertion hole 61 in the rod main body 63 with the axis of the mounting portion 92.

Accordingly, it is possible to easily connect and bond the implant 41 to the cervical vertebra rod plate 90, The present disclosure relates to subject matter contained in priority Japanese Patent Application Nos. 2000-289284, filed on Sep. 22, 2000, and 2000-302544, filed on Oct. 2, 2000, the contents of both of which are herein expressly incorporated by reference in their entireties.

What is claimed is:

1. A bone connecting system:
   a rod portion mounted to a cervical vertebra;
   a symmetrically-formed flat-shaped mounting portion provided in the rod portion and mounted to a cranium portion;
   a plurality of mounting holes provided in the flat-shaped mounting portion;
   a rod plate for a cervical vertebra in which the plurality of mounting holes are arranged in a symmetrical manner so as to be formed to be common between the right and left sides; and
   an implant screwed and inserted to the rod plate and a body of vertebra, comprising:
     a first fastening member having an engagement hole freely engaging with a head portion of the implant and a fastening groove; and
     a second fastening member provided with an insertion hole freely inserting the rod portion therethrough and a fastening groove, wherein
       a through hole penetrating in a direction crossing to the fastening groove in the first fastening member and a through hole penetrating in a direction crossing to the fastening groove in the second fastening member are provided fastening devices freely penetrating.

2. A bone connecting system according to claim 1, wherein
the fastening device is constituted by a bolt, and
a screw hole portion freely engaging with the bolt is formed in one end side of the through hole in the first fastening member or in one end side of the through hole in the second fastening member.

3. A bone connecting system according to claim 2, further comprising a first tool engagement portion in which an outer peripheral surface of a head portion in the bolt is formed in a polygonal shape.

4. A bone connecting system according to claim 3, wherein a second tool engagement portion is further provided in a top surface of the head portion in the bolt.

5. A bone connecting system according to claim 1, wherein the mounting portion is formed in a flat-shaped substantially fan shape, and the mounting portion is inclined with respect to the rod portion.

6. A bone connecting system according to claim 1, wherein a plurality of an angle adjusting and engaging portions are provided in a circular arc direction around a through hole of the first fastening member or the second fastening member, on a connecting surface between the first fastening member and the second fastening member.

7. A bone connecting system according to claim 1, wherein the implant screwed and inserted to the vertebral bone comprises:
a screw portion;
a cylindrical portion provided in a head portion of the screw portion; and
a polygonal tool engagement portion provided in a head portion of the cylindrical portion.

* * * * *